(12) United States Patent
Rehman et al.

(10) Patent No.: US 11,435,337 B2
(45) Date of Patent: Sep. 6, 2022

(54) DEVICE, SYSTEM, AND METHOD FOR ANALYZING TRANSFORMER OIL

(71) Applicant: King Fahd University of Petroleum and Minerals, Dhahran (SA)

(72) Inventors: Shafiqur Rehman, Dhahran (SA); Luai M. Alhems, Dhahran (SA); Ramsey Jadim, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 753 days.

(21) Appl. No.: 16/405,205

(22) Filed: May 7, 2019

(65) Prior Publication Data

US 2020/0355668 A1 Nov. 12, 2020

(51) Int. Cl.
| | |
|---|---|
| *G01N 1/14* | (2006.01) |
| *G01N 33/28* | (2006.01) |
| *H01F 27/12* | (2006.01) |
| *G01N 30/02* | (2006.01) |
| *G01N 1/24* | (2006.01) |

(52) U.S. Cl.
CPC .............. *G01N 33/287* (2013.01); *G01N 1/14* (2013.01); *G01N 30/02* (2013.01); *H01F 27/12* (2013.01); *G01N 2001/247* (2013.01); *G01N 2030/025* (2013.01)

(58) Field of Classification Search
CPC ........ G01N 33/287; G01N 1/14; G01N 30/02; G01N 2030/025; G01N 2001/247; G01N 2001/1418; G01N 2001/1427; G01N 2001/2229; G01N 2001/2232; G01N 2001/2238; G01N 2030/062; G01N 2030/065; H01F 27/12

USPC ............ 73/19.02, 19.1, 19.11, 23.41, 61.56, 73/61.59, 863, 863.21, 863.84, 864.21, 73/864.34, 864.81; 436/60, 174, 177, 436/180, 181; 422/521, 560, 561, 566
See application file for complete search history.

(56) References Cited

U.S. PATENT DOCUMENTS

2009/0067973 A1   3/2009  Eliuk et al.

FOREIGN PATENT DOCUMENTS

| CN | 2015022040 A | 3/2015 |
|---|---|---|
| CN | 204766522 | * 11/2015 |

(Continued)

OTHER PUBLICATIONS

Aroma Ready Products ; 5 ml Essential Oil Dispensing Syringe ; Product ; https://www.aromareadyproducts.com/bottles-and-containers/dispensing-tools.html ;Jan. 28, 2019 ; 2 Pages.

*Primary Examiner* — Robert R Raevis
(74) *Attorney, Agent, or Firm* — Oblon, McClelland, Maier & Neustadt, L.L.P.

(57) ABSTRACT

A system, device, and a method for determining a compound content in transformer oil are provided. The method includes positioning a syringe filled with transformer oil in the device to transfer the oil to a vial using the device. The device includes a stand, a threaded rod, a handle, a disc, and a syringe holder. The threaded rod is movable in a vertical direction by rotation of the handle and is configured to apply pressure via the disc on a plunger of the syringe positioned in the syringe holder to maintain an airtight connection between the vial and the device. The compound content is determined using a gas chromatograph by analyzing an aliquot extracted from a headspace gas of the vial.

13 Claims, 7 Drawing Sheets

(56) References Cited

FOREIGN PATENT DOCUMENTS

| | | | |
|---|---|---|---|
| CN | 105241987 | * | 1/2016 |
| CN | 205103167 | * | 3/2016 |
| CN | 105626249 A | | 6/2016 |
| CN | 105727394 | * | 7/2016 |
| CN | 106813947 | * | 6/2017 |
| CN | 207856048 | * | 9/2018 |
| JP | 3170485 | * | 5/2001 |
| JP | 2004209463 A | | 7/2004 |
| JP | 3846147 | * | 11/2006 |
| KR | 1914497 B1 | | 11/2018 |

* cited by examiner

DEVICE, SYSTEM, AND METHOD FOR ANALYZING TRANSFORMER OIL

BACKGROUND

Field of the Invention

This invention generally relates to a method and corresponding tool for transfer of liquids for analyzing. In particular, the invention provides a method and corresponding tool for sampling a transformer oil, transferring the transformer oil from a syringe to a vial and analyzing the transformer oil by gas chromatography for determining a compound content in the transformer oil.

Background of the Invention

Recently, serious failures of oil-filled electrical transformers were reported due to formation of Corrosive Sulphur Deposition (CSD) in the form of semi-conductive copper sulphide ($Cu_2S$) on internal components such as windings. See Yihua Qian and Wei Su, "Research on Influencing Factors of Corrosive Sulfur Attacking Copper in Insulating Oil and Prevention", IEEJ Transactions on Electrical and Electronic Engineering, Institute of Electrical Engineers of Japan, Vol. 8, pp. 546-549, 2013; D. H. Grant and P. Eng., "Quantification of reactive Sulphur in transformer oil", in IEEE Electrical Insulation Conference, Montreal, 2009, pp. 487-490; A. F. Holt, M. Facciotti, P. Amaro, R. C. D. Brown, P. L. Lewin, J. A. Pilgrim, G. Wilson and P. Jarman, "Silver corrosion in transformers", in annual Report Conference on Electrical Insulation and Dielectric Phenomena, IEEE Conference Publications 2013, pp. 448-45; R. Maina, V. Tumiatti, F. Scatiggio, M. Pompili, Senior Member, and R. Bartnikas, "Transformers Surveillance Following Corrosive Sulfur Remedial Procedures", IEEE Transactions on Power Delivery, Vol. 26, No. 4, pp. 2391-2397, 2011; Faheem Ahmed Khan and J. Sundara Rajan, "Experimental simulation of effects of copper Sulphide on insulation system of transformers", IEEE Transactions on Dielectrics and Electrical Insulation, IEEE Journals &Magazines, Vol. 22, No. 1, pp. 571-580, 2015; Faheem Ahmed Khan, J. Sundara Rajan, Mohd. Z. A. Ansari and Shahsadi Asra P, "An Experimental Study on the effects of DBDS in Transformer Oil of Power Transformers", in IEEE Advances in Power Conversion and Energy Technologies (APCET), 2012, Conference Publications, pp. 1-4; and J. Sundara Rajan, C. Jairam Naidu, K. Dwarakanath, A. K. Tripathy and Srilatha, "Monitoring of Total and Mercaptan Sulphur Under Combined Thermal Electrical Ageing of Paper-Oil Insulation System", in IEEE International Conference on Dielectric Liquids, 2008, IEEE Conference Publications, pp. 1-4, each incorporated herein by reference in their entirety. Formation of $Cu_2S$ can lead to many adverse consequences such as reducing the electrical resistivity of insulating paper; increasing dielectric losses, partial discharge, thermal instability and breakdown of the insulation system; and changing thermal conductivity of copper surface of windings which results in gases formation in the insulating oil. See A. Akshatha, K. Anjana, D. Ravindra, G. Vishwanath and J. Sundara Rajan, "Study of Copper Corrosion in Transformers due to Sulphur in Oil Using Chemical Methods", in Electrical Insulation and Dielectric Phenomena (CEIDP), 2012, IEEE Conference Publications, pp. 395-398, incorporated herein by reference in its entirety. However, direct or indirect damage of transformer components and the corresponding transformer failures can result in economic losses and pose a hazard to human life and adverse effects on the local environment. See S. Tenbohlen, T. Stirl, G. Bastos, J. Baldauf, P. Mayer, M. Stach, B. Breitenbauch and R. Huber, "Experienced-based Evaluation of Economic Benefits of On-line Monitoring Systems for Power Transformers", in Paris Conference 21, rue d'Artois, F-75008, Cigre; and Chan Loong Kwong, Chan Yan Tim, Leung Chun Kit and Ko Yik Yan, "From Great to Excellence—Approaching to Total Condition Based Management of Power Transformer under Smart Grid Operations", in 10th International Conference on Advances in Power System Control, Operation & Management, IET Conference Publications, pp. 1-6.

To protect the investment and prevent accidental losses in the power industry, transformer oils should be monitored regularly for early detection of corrosive sulphur formation. In oil filled power transformers, oil samples are taken out for laboratory analysis to determine the effect of heating on the oil and identify traces of corrosive sulphur formation in the transformer oil, if any. The formation of corrosive sulphur accelerates when the oil is overheated and/or when transformers are overloaded. With passage of time, elemental sulphur is released from the oil, which is present in the form of dibenzyl disulphide (DBDS) which reacts with the copper ions ($Cu^{++}$) released from the copper windings and copper plates. The elemental sulphur combines with the copper ions and forms copper sulfide ($Cu_2S$) which a conducting material. The $Cu_2S$, so formed, penetrates into insulating paper layers which keep the copper winding isolated from each other to avoid current conduction. The $Cu_2S$ keeps on depositing between the insulating paper layers and weakens the paper and makes it brittle. At times, these $Cu_2S$ layers become continuous and break the insulation and cause sparking inside the transformers. With continuous operation of the transformers and increasing temperatures inside, the transformers can explode and cause severe financial losses and human injuries and losses.

Saudi Arabia alone has a network of about 2058 power transformers installed in different parts of the Kingdom. See Saudi Electricity Company (SEC), Saudi Arabia. The cost of a power transformer varies from US $43,000 to US $50,000 per MVA. A transformer of 500 MVA costs US $21,500,000. According to TechSci Research report "Saudi Arabia Power & Distribution Transformers Market Forecast & Opportunities, 2020", the power and distribution transformers market in the Kingdom is projected to cross US $720 million by 2020. See Saudi Arabia Power and Distribution Transformers Market Forecast and Opportunities, 2020. Additionally, it may also cause injuries to the technicians and engineers if present in the vicinity. Hence utmost care needs to be taken to properly sample the oil samples from the transformers and analyze it for early detection of any corrosive sulfur formation. Early detection of corrosive Sulphur formation in the transformers helps to minimize arcing inside the transformers and ultimately avoids transformer failures.

However, it has always been a challenging task to obtain oil samples without atmospheric contamination. Accordingly, what is needed, as recognized by the present inventor, is a method and a tool for obtaining oil samples while minimizing contamination.

The foregoing "Background" description is for the purpose of generally presenting the context of the disclosure. Work of the inventor, to the extent it is described in this background section, as well as aspects of the description which may not otherwise qualify as prior art at the time of filing, are neither expressly or impliedly admitted as prior art against the present invention.

Accordingly it is one object of the present disclosure to provide a tool for transferring oil from syringe to vials with minimum contamination, for example by excluding air.

SUMMARY

The present disclosure relates to a method for determining a compound content in transformer oil. The method includes collecting a sample of oil from an oil tank of a transformer using a syringe; purging a vial with an inert gas; positioning the syringe in a syringe holder of an oil transfer device; inserting a needle of the syringe into the vial creating an airtight connection between the oil transfer device and the vial; operating a handle of the oil transfer device to fill the vial with oil from the syringe; releasing the inert gas overpressure in the vial; positioning the vial in a headspace sampler; extracting an aliquot from a headspace gas of the vial; injecting the aliquot into a gas chromatograph; and determining the compound content by analyzing the aliquot using the gas chromatograph.

The device includes a stand, a threaded rod, a handle, a disc, and a syringe holder. The stand includes an upper section, a base plate, and a frame. The threaded rod has a first distal end and a second distal end. The threaded rod is interconnected to the upper section of the stand via a supporting arm. The handle connected to the first distal end of the threaded rod. The disc is connected to the second distal end of the threaded rod. The syringe holder has an opening configured to hold a syringe in a vertical position and is connected to the frame of the stand. The threaded rod is movable in a vertical direction by rotation of the handle and is configured to apply pressure via the disc on a plunger of the syringe positioned in the syringe holder to fill a vial disposed on the base plate of the stand.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1:
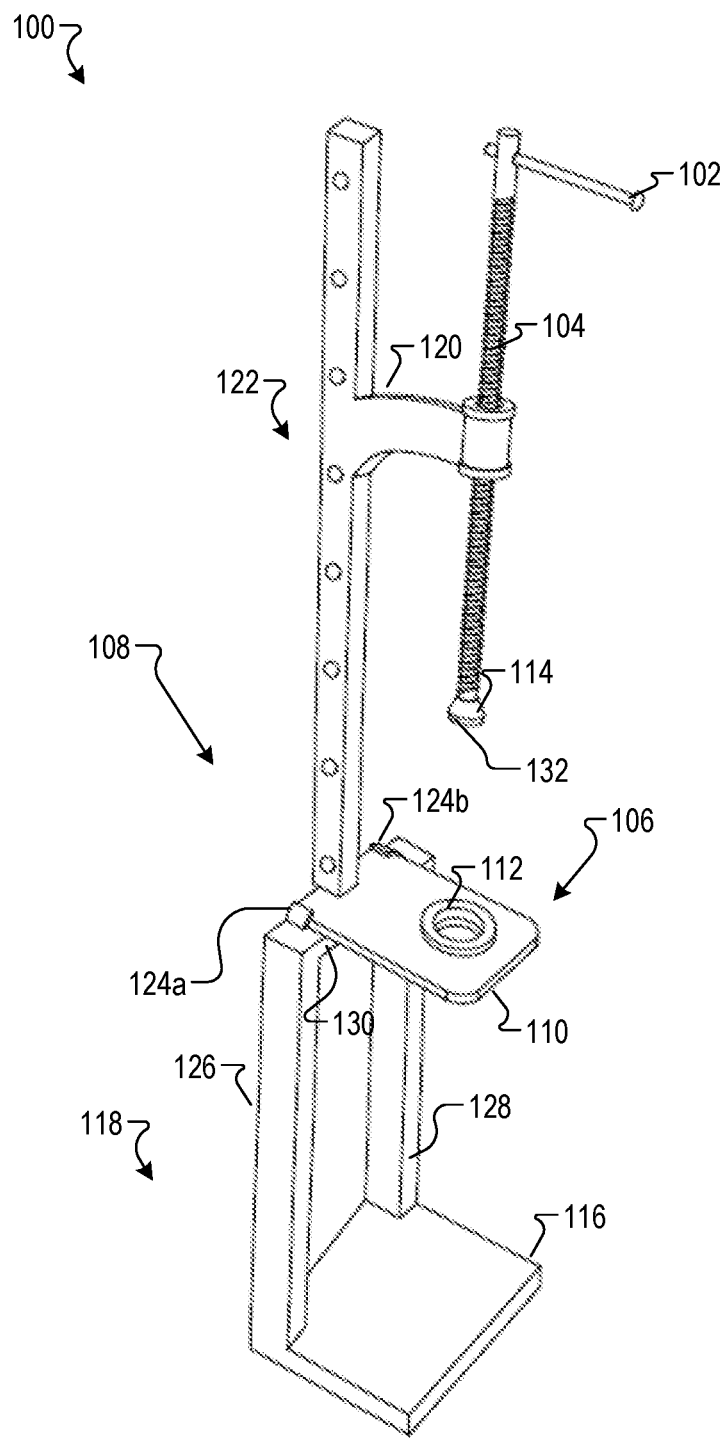
FIG. 1 is a schematic that shows a device for transferring oil from a syringe to a vial according to one example.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

Referring now to the drawings, wherein like reference numerals designate identical or corresponding parts throughout several views, the following description relates to a device (oil transferring tool) and associated methodology for transferring oil from a syringe to a vial.

Oil is transferred from the syringe to the vial for analysis in a headspace gas chromatography instrument in order to extract the gases from the oil before injection into the gas chromatography for column gas detection. The method described herein minimizes or eliminates contact with atmospheric air and thereby minimizes contamination.

FIG. 1 is a schematic that shows an oil transfer device 100 (referred to herein as device 100) for transferring oil from a syringe to a vial according to one example. The device 100 includes an arm or handle 102, a threaded rod 104, a syringe holder 106, and a stand 108. The syringe holder 106 includes a first plate 110 and a syringe base 112. The stand 108 holds the complete assembly of the device 100 (i.e., the syringe holder 106 and the threaded rod 104).

Figure 4:
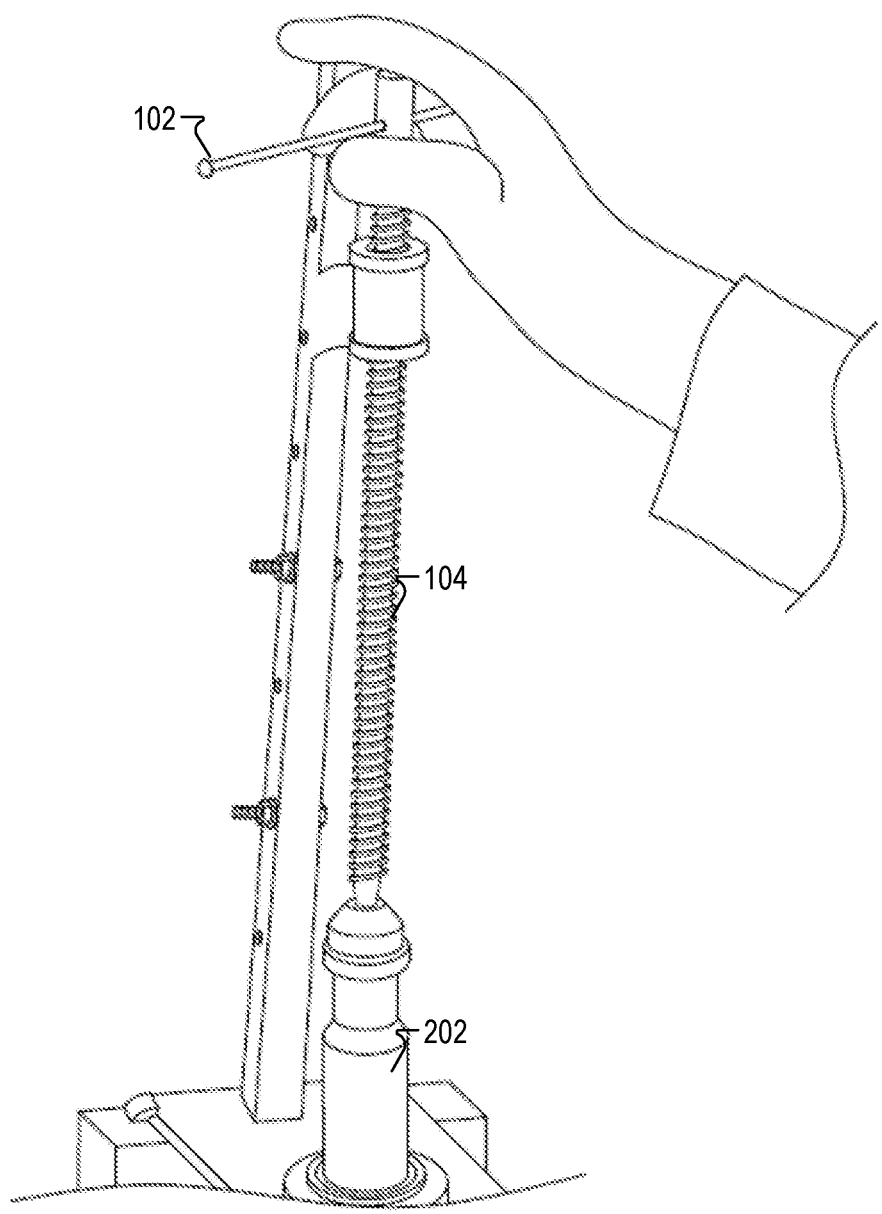
FIG. 4 is a magnified view of a handle of the device according to one example.

In operation, a syringe is held vertically in the syringe holder 106. The arm 102 is rotated which causes the threaded rod 104 to move along a vertical plane as shown in FIG. 4. The plunger of the syringe is depressed by the pressure caused from the contact with an end of the threaded rod 104.

The arm 102 is engageable with the threaded rod for imparting rotation to the threaded rod 104. The threaded rod 104 includes two distal ends. The arm 102 is connected to a first distal end of the threaded rod 104 (or upper section of the threaded rod 104). The arm 102 may be a non-threaded rod. In one example, the threaded rod 104 includes at the first distal end a hole in a horizontal direction configured to receive the arm 102. A first section of the arm or handle located at a first distal end of the arm has a larger diameter than the diameter of the hole of the threaded rod 104. The arm 102 is positioned such as a ¾ of the length of the rod is one side of the threaded rod. The arm 102 may be glided through the horizontal hole to adjust the position of the arm for user comfort and to provide a counter-weight mechanism.

A disc 114 is located at a second distal end of the threaded rod 104. For example, the disc 114 may be a round metal covered with a rubber sheet 132. The disc 114 may be glued to the threaded rod 104. In one example, the disc 114 is axially threaded to receive the second distal end of the threaded rod 104. The disc 114 may be exchangeable. In other words, a plurality of discs having different diameters may be used based on the size of the thumb press area of the syringe.

The stand 108 includes a base plate 116, a base frame 118 and an upper support section 122. The base plate 116 is disposed in a substantially parallel fashion with the first plate 110. The base plate 116 and the first plate are joined using the base frame 118. The base frame 118 includes a first vertical support column 126, a second vertical support column 128, and a horizontal support column 130. The horizontal support column 130 joins the first vertical support column 126 and the second vertical support column 128 in a "U" shape. The first vertical support column 126, the second vertical support column 128, and the horizontal support column 130 may be welded together. The base frame 118 is engaged with the base plate 116 by fixing the first vertical support column 126 and the second vertical support column 128 to a first corner and second corner of the base plate 116, respectively. For example, the first vertical support column 126 and the second vertical support column 128 are welded to the base plate 116.

The base plate 116 has a square shape of 15 cm by 15 cm. The threaded rod 104 has a length in a range of from 20 cm to 30 cm, or in the range from 22 cm to 28 cm, e.g., about 20 cm, 21 cm, 22 cm, 23 cm, 24 cm, 25 cm, 26 cm, 27 cm, 28 cm, 29 cm, or 30 cm. The first vertical support column 126 and the second vertical support column 128 have a length of 29 cm. In one example, the length of the horizontal support column matches the size of a first side of the base plate. For example, the horizontal support column may be 15 cm. The frame may have a thickness of 4 cm. The first plate 110 may have a rectangular shape. In one example, the first plate 110 has a dimension of 10 cm by 15 cm.

The first plate 110 may be attached to the base frame 118. In one example, the base frame 118 may include a first guided rail 124a and a second guided rail 124b. The first guided rail 124a and the second guided rail 124b are parallel to each other and are attached to a top surface of the horizontal support column 130. The syringe holder 106 may be attached to the stand 108 by gliding the first plate 110 into the respective guide rails. The syringe holder 106 may be exchanged by the user. Thus, the device 100 includes a plurality of syringe holders 106 to accommodate syringes of different sizes and shapes. For example, a second syringe holder may include a second plate having a round base of a diameter different than the first plate and may be used to accommodate a syringe of a different diameter (i.e., barrel diameter of the syringe).

Figure 7:
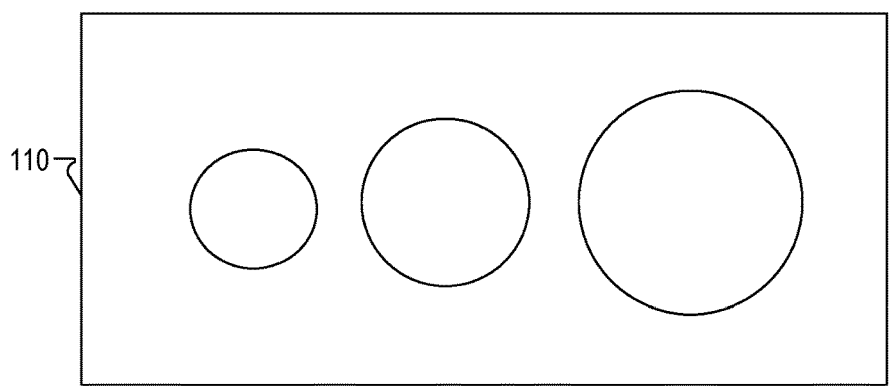
FIG. 7 is a schematic that shows a top view of a syringe holder according to one example.

The syringe holder 106 may include a circular syringe base. In other implementations, the syringe base 112 may be triangular, square, oval, or the like as understood by one of ordinary skill in the art. The first plate 110 may include multiple syringe bases. For example, the first plate 110 includes a first circular syringe base, a second circular syringe base, and a third circular syringe bases each having a different diameter as shown in FIG. 7. The user may glide the plate into the respective guide rails until the desired syringe base is aligned with the threaded rod. The diameter of the first circular syringe base may be 34.5 mm, the diameter of the second circular syringe base may be 44.5 mm, and the diameter of the third circular syringe base may be 24.5 mm.

The syringe base 112 may include a circular ring the size of the circular ring may be adjusted by tightening or untightening of a screw. For example, the circular ring may be a circular clamp (e.g., an O ring clamp).

Figure 9:
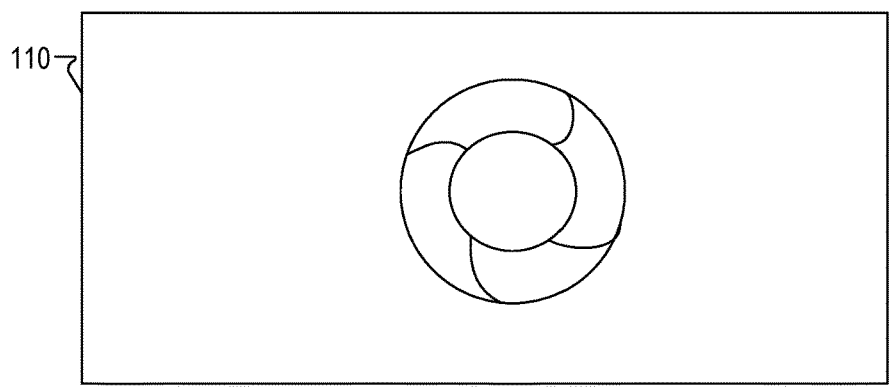
FIG. 9 is a schematic that shows a top view of the syringe holder according to another example.

In one implementation, the syringe base 112 includes an iris shutter mechanism to control the diameter of the base as shown in FIG. 9. The iris shutter mechanism includes a plurality of leaves arranged as an iris that open as would be understood by one of ordinary skill in the art. The iris opens to 35 mm diameter orifice or close to 5 mm diameter. The leaves are made of stainless sheet. Stainless sheet has a thickness in the range of 1 mm to 5 mm. Each leaf is provided with a pivot pin. The iris shutter mechanism also includes a drive ring. Rotating the drive ring causes the leaves to change the orifice size. In operation, the iris shutter mechanism is opened, the syringe is inserted, and then the drive ring is turned to close the leaves until the distal end of the leaves opposite to the end including the pivot pin is in contact with the barrel of the syringe.

The syringe base 112 is made of an elastic material configured to expand to accommodate syringes of multiple barrel diameters. For example, the first plate 110 may include an opening of 25 mm. An elastic sleeve of 15 mm is attached to the inner surface of the opening. Thus, the syringe base 112 accommodates syringes having a barrel diameter in the range of from about 15 mm to about 25 mm.

The first plate 110 may be screwed to the base frame 118. For example, the horizontal support column 130 includes two screw holes at each end.

The upper support section 122 may have a rectangular shape and may be formed from solid metal. In another example, the upper support section 122 may be formed from a hollow metal. In one example, the stand is constructed from aluminum, although other types of material may be used.

The threaded rod 104 is held to the upper support section 122 of the stand 108 via a support arm 120. The support arm 120 includes a first end and a second end. The first end of the support is connected to the upper support section 122. The threaded rod screws into the support arm 120 which has a single appropriately threaded hole at a second end. The support arm 120 may be movable in the vertical direction to accommodate syringes of different length. The support arm 120 may be fixed to the upper support section 122 via screws. The support arm 120 is fixed in an angle with respect to the upper support section. For example, the upper support section includes a plurality of screw holes spaced by a predetermined distance (e.g., 1 cm).

In one example, the upper support section 122 may include a collapsing/expanding section that includes a plurality of apertures. The apertures are sized to receive a pin. The apertures and pin allow for adjustment of the collapsing/expending section to change the position of the support arm 120. The upper support section 122 may be formed by two hollow sections with one section telescopically and nestedly received within the second section. Thus, the height of the arm with respect to the base plate 116 is adjusted by expanding or collapsing the sections and securing the height with the pin.

Figure 8:
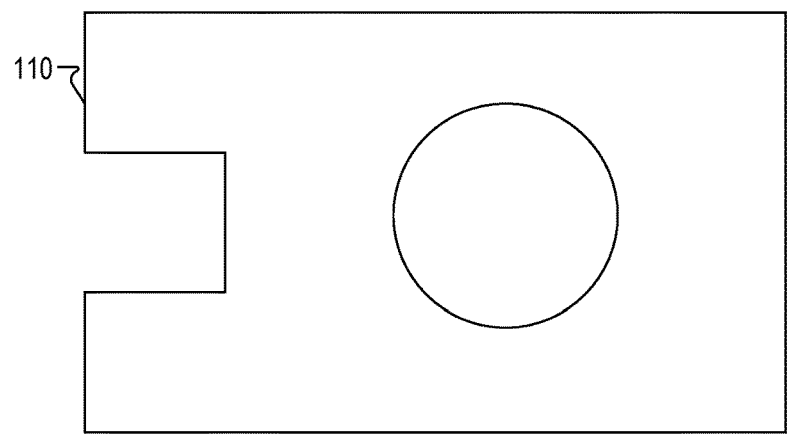
FIG. 8 is a schematic that shows a top view of the syringe holder according to another example.

The upper support section 122 is in direct contact with the horizontal support column 130. The first plate 110 includes a groove (i.e., a cut) on a side having a shape reciprocal to a cross section of the upper support section 122 as shown in FIG. 8. For example, the horizontal support column has a rectangular cross-section and the first plate 110 has a cut having a rectangular shape at a first side. The upper support section 122 may be welded or glued to the top surface of the horizontal support column 130.

In one implementation, the upper support section 122 may be clamped to the horizontal support column 130. A distance between a bottom surface of the upper support section 122 and the upper surface of the horizontal support column 130 is adjustable. For example, the thickness may be adjusted to be equal to the thickness of the first plate 110. The first plate 110 may be inserted between the bottom surface of the upper support section 122 and the upper surface of the horizontal support column 130.

In one implementation, the arm 102 is connected to an electrical motor (not shown) configured to rotate the arm to move the threaded rod 104 in the vertical direction. The electrical motor may be battery operated and/or solar rechargeable to facilitate operation in the field.

In one implementation, the stand 108 may hold two or more threaded rods and/or two or more syringe holders. In one example, the base plate 116 may be rotatable. The base plate 116 has a circular shape and includes multiple grooves. Each groove is configured to hold a vial. Once the user has filled a first vial, the base plate 116 is rotated and a second vial is filled.

Figure 2:
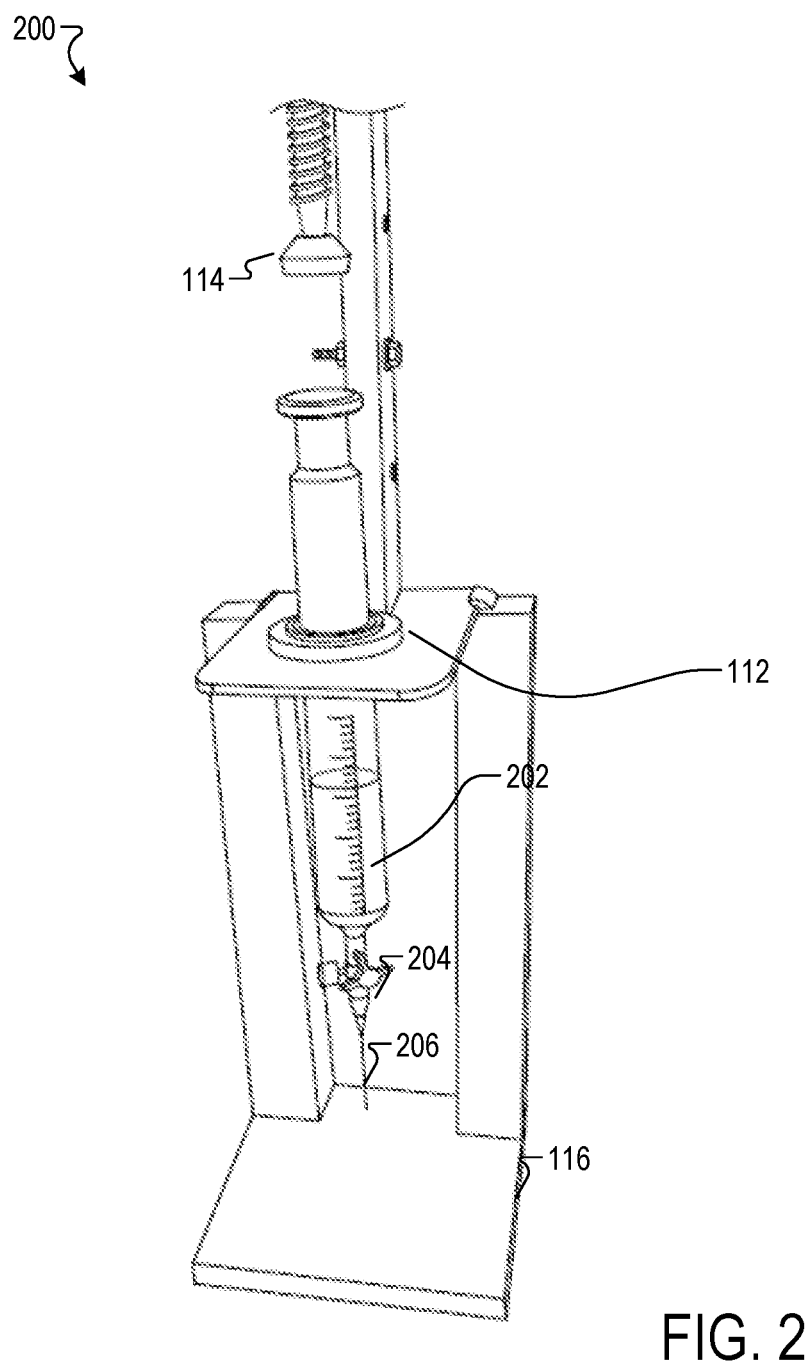
FIG. 2 is a schematic that shows the syringe positioned in the device according to one example.

FIG. 2 is a schematic 200 that shows a syringe 202 positioned in the device 100 according to one example. The barrel or tubular body of the syringe is made of a clear material. For example, the body may be made of a clear plastic material or glass. The syringe 202 may be a glass syringe having a capacity in the range from 20 ml to 100 ml, in the range from 30 ml to 90 ml, or in the range from 40 ml to 80 ml. The syringe may have a capacity of 50 ml. The syringe includes a three way valve 204 at a distal end of the barrel of the syringe 202 to control the flow of oil from the syringe to the vial via a needle 206. In one implementation, the syringe 202 includes one valve at the distal end to control the flow from the interior of the barrel of the syringe while preventing the flow in the opposite direction.

Figure 3:
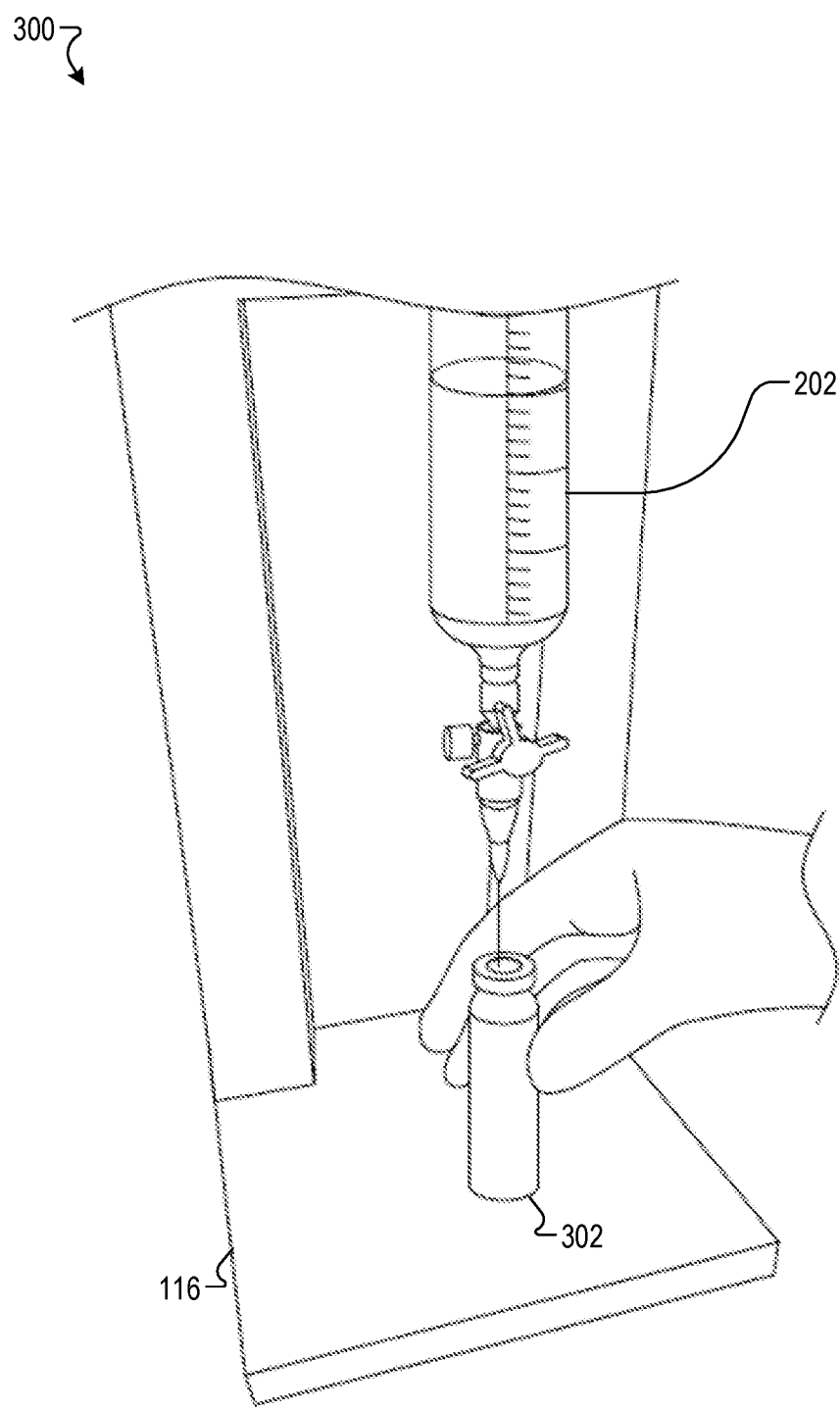
FIG. 3 is a schematic that shows a vial being filled using the device according to one example.

FIG. 3 is a schematic 300 that shows a vial 302 being filled using the device 100 according to one example. The vial 302 is positioned on the base plate 116. The base plate 116 may include a circular groove having a diameter that matches a diameter of the lower section of the vial 302. The base plate 116 may include a heating and/or cooling plate. Further, the base plate 116 may include a scale and a display area. The scale detects a weight of the vial positioned in the circular groove. The detected weight is displayed in the display area.

Figure 5:
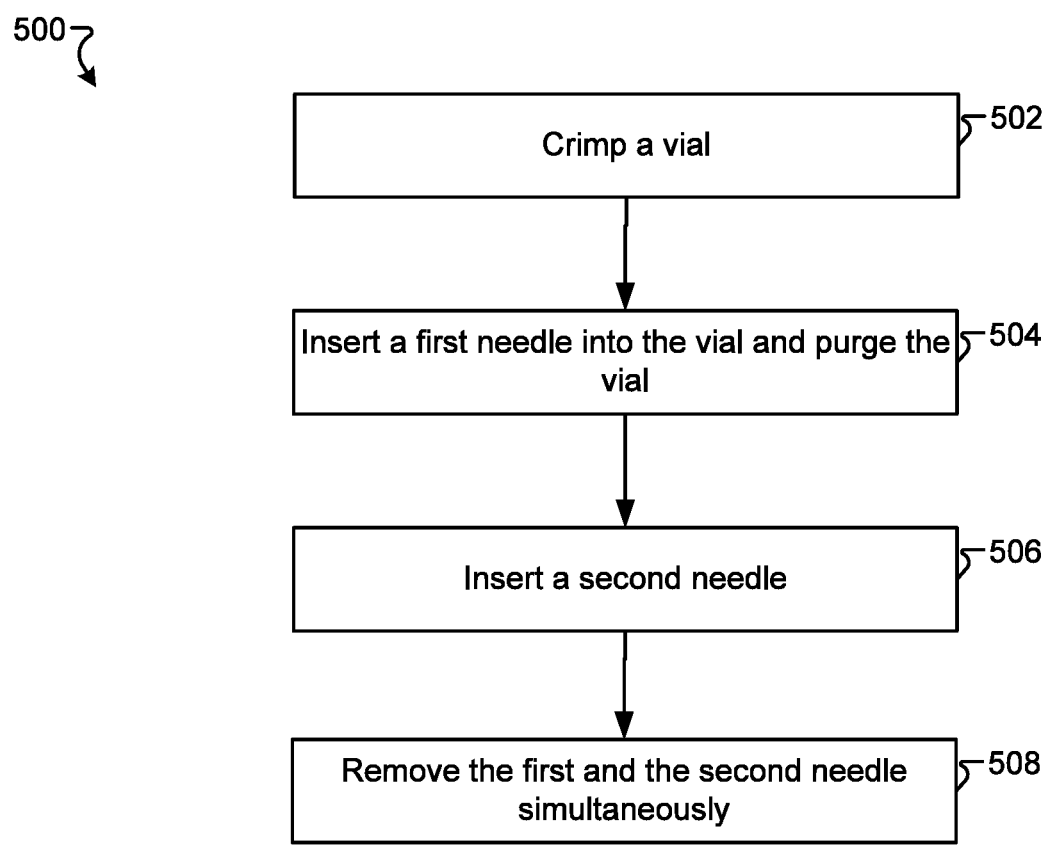
FIG. 5 is a flowchart for a method for preparing a vial according to one example.

FIG. 5 is a flowchart for a method 500 for preparing a vial according to one example. At step 502, the vial is crimped with a septum (the vials may be of different sizes depending on the requirement of the testing instrument). For example, a 20 ml vial is crimped. At step 504, a needle is inserted through the septum of the vial and argon gas is purged. At step 506, a second needle is inserted simultaneously through the septum of the vial. The second needle is used to release the argon gas overpressure. Note that the pressure in the vial up to step 506 is atmospheric pressure.

At step 508, the first needle and the second needle are removed simultaneously. Then, the vial (pre-purged) is weighed or the weight shown in the display area is recorded at step 510. The vial is ready for oil transfer.

Figure 6:
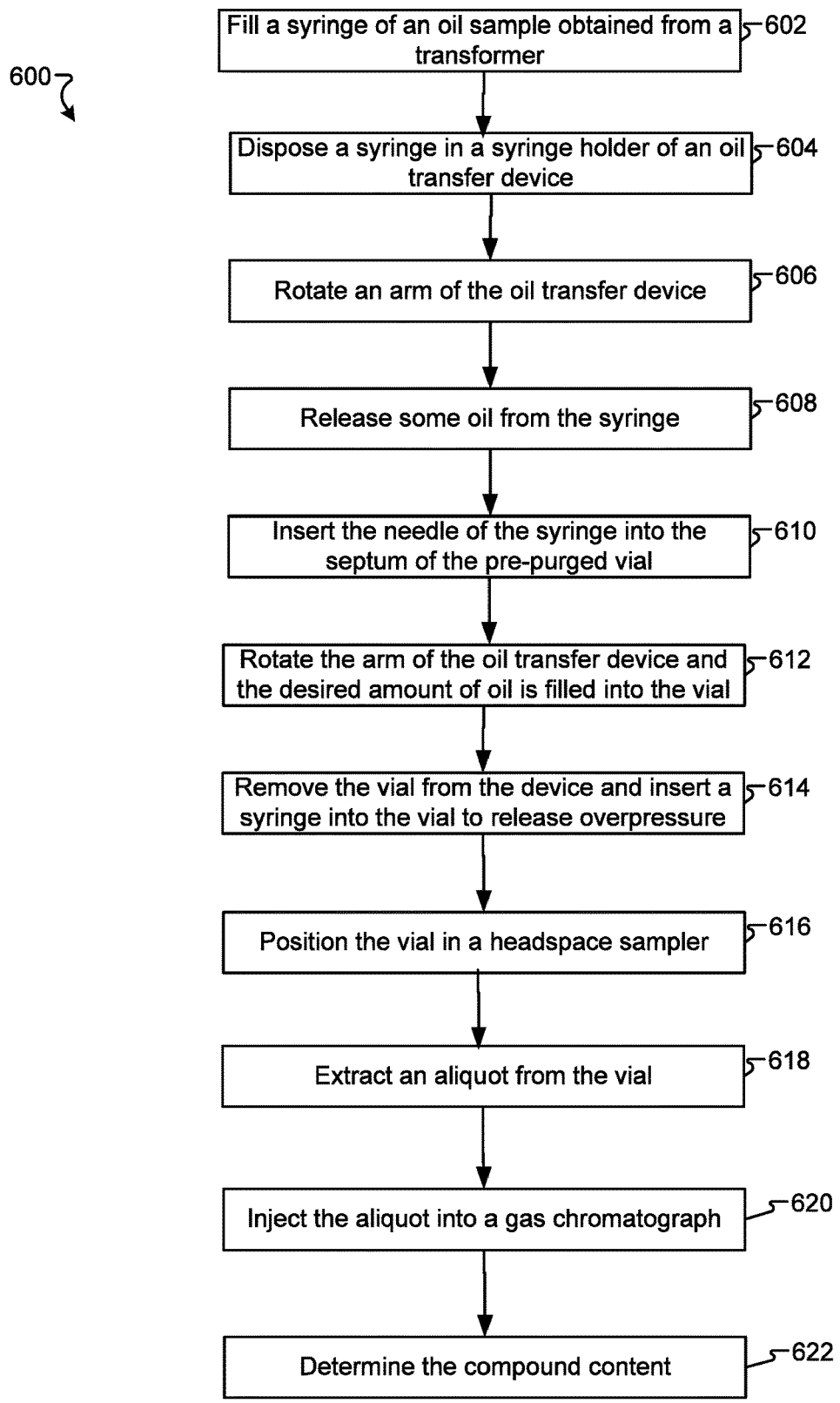
FIG. 6 is a flowchart for a method for transferring oil from a syringe to a vial according to one example.

FIG. 6 is a flowchart for a method 600 for detecting corrosive Sulphur in a transformer according to one example.

At step 602, a sample of oil from an oil tank of a transformer is collected using the syringe. For example, the oil tank may be opened or pierced. Then, a sample is drawn using the syringe. The plunger of the syringe is fully depressed until a connection between the needle of the syringe and the oil is made.

In one implementation, the oil tank is maintained under positive pressure. Two or three liters of oil may be flushed before taking the oil sample. A tube (e.g., Tygon tube) is connected to the syringe via a luer lock connector. A stopcock is securely tightened on the syringe luer lock. Next, the syringe port is opened by turning the stopcock handle toward the side port to fill the syringe with oil (30 ml to 50 ml). The front port is then closed by moving the nylon stopcock handle toward the tygon tube and positioning the syringe in a vertical position. While the glass syringe is in vertical position and the front port is in an off position, the oil is emptied and any air bubbles is purged until all of the oil is cleared from the syringe. These steps may be repeated 2 to 3 times before taking the oil sample.

To take the oil sample, the side port is closed and the transformer reservoir pressure is allowed to push the plunger of the syringe until the syringe is filled up to 40 ml (e.g., for a 50 ml syringe). Then, the stopcock handle is turned to the off position and the syringe is separated from the tubing. The syringe is filled without puling on the plunger to avoid subjecting the sample to a vacuum which can degas the oil and lead to inaccurate test results. At step 604, the syringe (e.g., a glass syringe) is disposed in the syringe holder. The syringe is filled with an oil sample obtained from a transformer. The syringe may be jointed with a needle via a three-way valve. In one example, the syringe may have a capacity of 50 ml.

At step 606, the handle of the threaded rod is rotated until a first end of the piston comes into contact with a thumb press area of the glass syringe as shown in FIG. 4.

At step 608 a waste beaker is disposed under the needle of the syringe. The handle 102 of the device 100 is rotated to release some oil for removing air bubbles in the needle.

At step 610, the needle of the syringe is inserted through the septum of the pre-purged crimped vial.

At step 612, the handle 102 is rotated until the vial is filled up with the predetermined amount of oil.

At step 614, the vial is removed from the device assembly. Then, a needle is inserted through the septum of the vial to release the argon gas overpressure. The oil-filled vial is weighed. The weight of the empty vial is subtracted to get the mass of oil in the vial before placing it in the headspace.

In one implementation, steps 604-616 are performed on the field. Therefore, the syringe is not shipped or transported to the laboratory which minimizes contamination.

At step 616, the vial is placed in a headspace sampler to extract an aliquot. For example, the headspace sampler may include a mixing function and a heat-ahead function. The vial is mixed by shaking to obtain equilibrium quickly. The headspace sampler includes a thermostatic vial chamber that provides a uniform temperature distribution. Techniques for extracting the aliquot may include a headspace sorptive extraction (HSSE) technique and a stir bar sorptive extraction (SBSE) technique.

At step 618, the aliquot is extracted from the headspace gas. Then, the aliquot is injected into a gas chromatograph at step 620. Then, the Sulphur content is determined at step 622 using the gas chromatograph (GS).

The gas chromatograph measures the gas concentration levels of one or more gases (e.g., fault gases) contained in the headspace. For example, the one or more gases may include hydrogen, oxygen, nitrogen, methane carbon monoxide, carbon dioxide, ethylene, ethane, acetylene, dibenzyl disulfide, and the like. The gas chromatograph identifies the gases present in the sample and also the quantitative amounts. The one or more gases are associated with certain fault conditions (e.g., overheating, corona, arcing, and overheating). For example, abnormal level of acetylene indicates arcing. Corona is detected by elevated levels of hydrogen.

The aliquot is injected into the injection port of the gas chromatograph and carried to the column or columns. In the column, the sample is separated on a long narrow column with a non-volatile stationary phase. In one example, the column selectively retards the sample gases. Sample molecules enter a detector that functions as a transducer which generates an electrical signal that is measured and recorded. Detected compounds produce peaks in the recoded signal. The detector may include a thermal conductivity detector for atmospheric gases and a flame ionization detector for hydrocarbons and oxides of carbon.

Further, method 600 is repeated on a regular basis to determine a rate of change in the concentration of the gases. Samples may be tested on a daily basis, a weekly basis, or the like. Results from the gas chromatography are used with other methods to evaluate electric faults within the transformer. In one example, a Duval triangle analysis may be used to monitor fault zones over time. The results may be monitored using a processor. A warning or an alert may be generated when one or more components exceed a threshold level. The processor may change a testing frequency when a level of a compound is within a predetermined percentage of the threshold level.

The oil transfer tool described herein assures uncontaminated transfer of transformer oil in to the vials to be used in experimental tests by providing an airtight connection between the vial and the syringe. The tool provides for precise transfer of oil without air contamination. Further, the tool minimizes contamination due to human errors while manipulating transformer oil. The uncontaminated oil samples produce nearly quantitative results which assess the conditions of the oil inside the transformer with 99.99% accuracy. The tool described herein is portable. The operators/technicians can take the device to the site and can collect the oil sample from the live transformer.

The oil can be tested for its electrical and chemical properties to make sure it is suitable for continued use. Tests may include dissolved gases, furan content, water content, acidity (Neutralization Value) and PCB analysis. Tests for general electrical and physical properties may include color, appearance, breakdown voltage, dielectric dissipation factor, resistivity, sediments, sludge, flash point, pour point, density, kinematic viscosity. Testing may be by the protocols described in any of ASTM D1500, D 877, ASTM D1816, ASTM D3612, ASTM D7151, ASTM D92, ASTM D971, ASTM D5837, ASTM D1533, ASTM D924, ASTM D974, ASTM D2668, ASTM D4059, ASTM D1298, ASTM D1524, ASTM D1169, ASTM D1524, VDE370-5/96, OVE EN60156, IEC 60156/97, ASTM1816-04-1, ASTM1816-04-2, ASTM877-02A, ASTM877-02B, AS1767.2.1, BS EN60156, NEN 10 156, NF EN60156, PA SEV EN60156, SABS EN60156, UNE EN60156 and IS:6792 of 1972.

Depending on the results of the analysis the oil condition can be improved by filtration and treatment. Alternately the oil may be replaced or the transformer retired from, service.

Numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method for determining a compound content in transformer oil, the method comprising:
    collecting a sample of oil from an oil tank of a transformer using a syringe;
    purging a vial with an inert gas;
    positioning the syringe in a syringe holder of an oil transfer device;
    inserting a needle of the syringe into the vial creating an airtight connection between the oil transfer device and the vial;
    operating a handle of the oil transfer device to fill the vial with oil from the syringe;
    releasing the inert gas overpressure in the vial;
    positioning the vial in a headspace sampler;
    extracting an aliquot from a headspace gas of the vial;
    injecting the aliquot into a gas chromatograph; and
    determining the compound content by analyzing the aliquot using the gas chromatograph, wherein the oil transfer device includes a stand having an upper section, a base plate, and a frame, the threaded rod having a first distal end and a second distal end, the threaded rod being interconnected to the upper section of the stand via a supporting arm, the handle being connected to the first distal end of the threaded rod, a disc being connected to the second distal end of the threaded rod, and a syringe holder having an opening configured to hold a syringe in a vertical position and is connected to the frame of the stand, the threaded rod being movable in a vertical direction by rotation of the handle and is configured to apply pressure via the disc on a plunger of the syringe positioned in the syringe holder to maintain the airtight connection between the oil transfer device and the vial,
    wherein the disc is covered with a rubber material.

2. The method of claim 1, wherein purging the vial includes:
    injecting the inert gas into the vial via a first needle,
    inserting simultaneously a second needle into the vial to release the inert gas overpressure, and
    removing the first and the second needle.

3. The method of claim 1, wherein the compound is sulfur.

4. The method of claim 1, wherein the handle is connected to an electrical motor configured to rotate the arm to move the piston in the vertical direction.

5. The method of claim 1, wherein an opening of the syringe holder has an adjustable diameter.

6. The method of claim 5, wherein the adjustable diameter is in a range from 15 mm to 35 mm.

7. The method of claim 5, wherein the syringe holder includes an exchangeable plate including the opening.

8. The method of claim 7, wherein the syringe holder further includes an iris mechanism for controlling a diameter of the opening, the iris mechanism including a plurality of leaves connected to a drive ring.

9. The method of claim 7, wherein the plate includes a cut at a first side edge having a profile corresponding to a cross-section of the upper section of the stand.

10. The method of claim 9, wherein the cut has a rectangular shape.

11. The method of claim 1, wherein the threaded rod has a lower section and an upper section, the upper section including an horizontal opening adapted to hold the handle in an horizontal position.

12. The method of claim 1, wherein the frame has a U shape and includes two vertical support columns and a horizontal support column.

13. The method of claim 1, wherein the base plate includes a circular groove configured to hold the vial.

* * * * *